United States Patent [19]

Nonn

[11] Patent Number: 5,107,044

[45] Date of Patent: Apr. 21, 1992

[54] PROCESS FOR BROMINATION OF BIPHENYL WITH BRCL

[75] Inventor: Alain Nonn, Pfastatt, France

[73] Assignee: Rhone-Poulenc Chimie, Cedex, France

[21] Appl. No.: 586,388

[22] Filed: Sep. 20, 1990

Related U.S. Application Data

[63] Continuation of Ser. No. 371,030, Jun. 26, 1989, abandoned.

[30] Foreign Application Priority Data

Jun. 27, 1988 [FR] France .................. 88 08583

[51] Int. Cl.$^5$ .............................. C07C 17/12
[52] U.S. Cl. ...................... 570/206; 570/182; 570/183; 570/190
[58] Field of Search ............ 570/188, 206, 208, 182, 570/183, 190, 192

[56] References Cited

U.S. PATENT DOCUMENTS

| | | | |
|---|---|---|---|
| 2,019,015 | 10/1935 | McCullough | 570/206 |
| 2,607,802 | 8/1952 | Britton et al. | 570/206 |
| 3,845,146 | 10/1974 | Moore | 570/206 |

FOREIGN PATENT DOCUMENTS

| | | | |
|---|---|---|---|
| 0331549 | 9/1989 | European Pat. Off. | 570/206 |
| 1933486 | 1/1971 | Fed. Rep. of Germany | 570/206 |
| 2144259 | 3/1972 | Fed. Rep. of Germany | 570/206 |
| 2950877 | 6/1981 | Fed. Rep. of Germany | 570/206 |

OTHER PUBLICATIONS

Olah et al., "J. Amer. Chem. Soc.", vol. 86(6), pp. 1039, 1046 (1964).

*Primary Examiner*—Werren B. Lone
*Attorney, Agent, or Firm*—Finnegan, Henderson, Farabow, Garrett and Dunner

[57] ABSTRACT

A process for the bromination of biphenyl, particularly for the preparation of 4-bromobiphenyl or of 4,4'-dibromobiphenyl. The process comprises reacting biphenyl with BrCl. The BrCl may be formed in situ in the reaction medium or may be formed before reaction with biphenyl.

9 Claims, No Drawings

PROCESS FOR BROMINATION OF BIPHENYL WITH BRCL

This application is a continuation of application Ser. No. 07/371,030, filed June 26, 1989, now abandoned.

The present invention relates to a process for bromination of biphenyl with BrCl, and more particularly relates to a process for preparing 4-bromobiphenyl or 4,4'-dibromobiphenyl.

4-Bromobiphenyl is a product capable of many applications. It can be employed in the manufacture of agrochemical or pharmaceutical compounds. It can also be used for the preparation of liquid crystals.

4,4'-Dibromobiphenyl is a compound whose hydrolysis yields 4,4'-dihydroxybiphenyl, the latter product being useful as a monomer for thermotropic polymers.

Thus, both 4-bromobiphenyl and 4,4'-dibromobiphenyl are products which are useful in industrial applications.

One of the problems which arises in preparation of these compounds is that of ring position selectivity, since the object is to obtain products brominated in the 4- or 4,4'-positions.

Therefore, there is a need in the art for a process which is simple, i.e., can be conducted in mild conditions, is selective and has fast kinetics.

It is an object of the present invention to develop a process meeting the above requirements.

The process according to the invention for bromination of biphenyl is characterized in that biphenyl is reacted with BrCl.

The process of the invention makes it possible to obtain yields of at least 60% at ambient temperature and with reaction times on the order of one hour.

Other characteristics and details of the invention will become more clearly apparent upon reading the description and the working examples which follow, no limitation being implied.

A main feature of the process of the invention lies in the use of BrCl as the brominating agent. The process can be implemented according to two alternative embodiments.

A first alternative embodiment comprises forming BrCl before its reaction with biphenyl. In this case, it is possible to employ any known means for manufacturing BrCl.

By way of example, it is possible to form BrCl by bubbling chlorine into HBr or by the action of HCl on an N-bromo derivative such as, for example, N-bromo-N-methylacetamide, N,N-dibromohydantoin, or N-bromosuccinimide in aqueous solution or in organic solution. A preferred method of forming BrCl comprises bubbling chlorine into $Br_2$ in a solvent solution of $CCl_4$, $CHCl_3$, $CH_2Cl_2$ or aqueous HCl, for example.

A second alternative embodiment, which is the preferred embodiment, comprises forming BrCl in situ, i.e., BrCl is formed in the reaction medium as the reaction with biphenyl takes place.

In this second embodiment, bromine is preferably introduced into the reaction medium in a first step. In a second step, chlorine is added and the reaction kinetics are simultaneously accelerated.

In accordance with the invention, it would also be possible to introduce bromine and chlorine simultaneously while continually maintaining an excess of bromine relative to chlorine.

In both the first and second alternative embodiments mentioned above, it is preferable to cool the reaction medium to a temperature below or equal to 5° C. In the case of the second alternative embodiment with delayed introduction of bromine and chlorine, this cooling may be carried out after the introduction of bromine and before that of chlorine. The cooling lasts for at least a part of the reaction, preferably throughout its duration. Once the reaction is complete, the temperature is allowed to rise again. Cooling enables BrCl to be kept in a liquid form which makes it easier to control the reaction completely.

In all cases, it is necessary to operate with at least 0.5 equivalent of $Br_2$ relative to the biphenyl in the case of a monobromination and of at least 1 equivalent of $Br_2$ relative to the biphenyl in the case of a dibromination. It is quite possible to operate with an excess of bromine relative to the quantities just mentioned. To avoid the interfering chlorination reaction when BrCl is formed in situ, the quantity of chlorine should preferably be smaller than or equal to that of bromine. The specific ratio of bromine to chlorine is selected based on the desired degree of bromination.

The reaction preferably takes place in a medium comprising a solvent. A large number of solvents can be employed and it is preferable that the solvents utilized be inert to bromine and chlorine. The solvent may be selected from the group consisting of halogenated or unhalogenated aliphatic, alicyclic and aromatic hydrocarbons, ethers and nitro solvents.

Examples of usable solvents include hexane, carbon tetrachloride, dichloromethane, trichloromethane, dibromoethane, dichlorobenzene, nitrobenzene, isopropyl ether, hexyl ether and butyl ether.

EXAMPLE 1

The following were placed in a 150-ml round-bottom flask equipped with a thermometer sheath, a dropping funnel, a chlorine inlet dip tube, a two-bladed mechanical stirrer and a condenser connected to a column for scrubbing and neutralizing acids:

15.4 g of biphenyl (0.1 mol),
50 ml of dichloromethane, and
27.2 g of bromine (0.17 mol), that is a 70% excess relative to the stoichiometric quantity needed for a dibromination.

These were then cooled to 5° C. and 0.17 moles of chlorine were introduced at a flow rate of 2.66 liters/hr. for 86 minutes while the temperature was kept below 5° C.

The temperature was then allowed to rise again to ambient and the mixture was kept stirred for 1.5 hours.

The excess unreacted bromine was neutralized by adding a 10% strength aqueous sodium sulphite solution.

After addition of dichloromethane in a sufficient quantity to dissolve the precipitate formed during the reaction, separation was carried out, the organic phase was dried and the solvent was then evaporated off. The solid obtained was dried in an oven at 70° C. and was then analyzed by gas phase chromatography. Its mass was 31.2 g, and its composition by weight was as follows:

87.3% (4,4'-diBr), that is 87.3% conversion yield (CY) (moles of product divided by moles of biphenyl converted)
0.7% (4-Br) 0.9% CY
0.12% 2-bromobiphenyl 0% biphenyl, degree of conversion (DC)=100%

EXAMPLE 2

The operating method employed was the same as in Example 1, but this time charging:
15.4 g of biphenyl (0.1 mol),
50 ml of dichloromethane,
22.4 g of bromine (0.14 mol), that is a 40% excess as defined above, and
0.13 mol of chlorine.

The chlorine was introduced at 2.66 liters/hr. over 66 minutes. After this introduction of chlorine, the excess bromine was neutralized and the subsequent procedure was as described in Example 1.

The solid product recovered had a mass of 28.22 g and the following composition by weight:

| 77.7% (4,4'-diBr) | CY = 70.3% |
|---|---|
| 1.4% (4-Br) | CY = 1.7% |
| 0% biphenyl- | DC = 100% |

EXAMPLE 3

The following were charged into a 250-ml three-necked flask with magnetic stirring and equipped as in Example 1:
30.8 g (0.2 mol) of biphenyl and
100 ml of dichloromethane.
35.2 g (0.22 mol) of bromine were added over 30 minutes at 0° C., with stirring; 15 minutes after the beginning of the addition of bromine, 4.71 g (0.21 mol) of chlorine were added over, a period of 2 hr. 15 min.
30 minutes after the end of the addition of chlorine, the brominating species was neutralized with a sodium sulphite solution.

Results

DC=100%
reaction yield (RY) (4,4'-diBr) (moles of product divided by moles of starting biphenyl)=74.4%
RY (4-Br)=1.5%

EXAMPLE 4

The following were charged into the same apparatus as in the preceding example:
30.8 g of biphenyl (0.2 mol), and
80 ml of dichloromethane.

In parallel, BrCl was prepared by adding 16.4 g of chlorine (0.23 mol) to 35.2 g of bromine (0.22 mol) dissolved in 80 mol of dichloromethane at 0° C. for 1 hour.

BrCl was then added dropwise over a period of 2 hrs., 55 min. to the biphenyl solution at 0° C. 15 minutes after the end of the addition, neutralization was carried out with an aqueous sodium sulphite solution.

Results

DC=100%
RY (4,4'-diBr)=72.2%
RY (4-Br) 3.0%

EXAMPLE 5

The operating method followed was the same as in Example 1, but introducing initially:
0.1 mol biphenyl,
50 ml of dichloromethane,
0.053 mol of bromine, and
0.05 mol of chlorine.

The chlorine was introduced at the same flow rate as in Example 1, over 26 minutes. After this introduction, the excess bromine was neutralized and the procedure was then conducted as before.

A mass of 23.5 g of the following composition by weight was recovered:

| biphenyl | 13% |
|---|---|
| 4-bromobiphenyl | 73.5% |
| 4,4'-dibromobiphenyl | 8.5% | that is,

| biphenyl | DC = 81% | |
|---|---|---|
| 4-bromobiphenyl | RY = 74% | CY = 91.4% |
| 4,4'-dibromobiphenyl | RY = 6% | CY = 7.4% |

COMPARATIVE EXAMPLE 6

The procedure was as in Example 1, but adding twice as much bromine, at ambient temperature and without adding chlorine; after 21 hours a mass of 25.8 g of the following composition by weight was obtained:

| 37% of 4,4'-dibromobiphenyl, | CY = 30.6% |
|---|---|
| 57% of 4-bromobiphenyl, | CY = 63.1% |
| 4% of 2-bromobiphenyl, | CY = 4.4% |
| 1% of biphenyl, | DC = 98.2% |

What is claimed is;

1. A process for selectively brominating biphenyl in the para positions comprising the step of reacting biphenyl with BrCl in a reaction medium for a time sufficient to form 4-bromobiphenyl, 4-4'-dibromobiphenyl or a mixture thereof.

2. The process according to claim 1, wherein the reaction takes place in a medium comprising a solvent.

3. The process according to claim 2, wherein BrCl is formed in situ in the reaction medium during the reaction with biphenyl.

4. The process according to claim 1, wherein BrCl is formed before its reaction with biphenyl.

5. The process according to claim 2, wherein the solvent is selected from halogenated aliphatic hydrocarbons, unhalogenated aliphatic hydrocarbons, alicyclic hydrocarbons, aromatic hydrocarbons, ethers and nitro solvents.

6. The process according to claim 3, wherein the bromine is introduced into the reaction medium in a first step and chlorine is introduced in a second step.

7. The process according to claim 3, wherein bromine and chlorine are introduced simultaneously into the reaction medium.

8. The process according to claim 3, wherein the reaction is conducted with an excess of bromine relative to chlorine.

9. The process according to claim 1, wherein the reaction mixture is brought to a temperature not greater than 5° C. during at least a part of the reaction.

* * * * *